United States Patent [19]

Kanesaka

[11] Patent Number: 5,381,790

[45] Date of Patent: Jan. 17, 1995

[54] ELECTROPHYSIOLOGY APPARATUS

[76] Inventor: Nozomu Kanesaka, 36 Cathy Rd., Hillsdale, N.J. 07642

[21] Appl. No.: 80,009

[22] Filed: Jun. 23, 1993

[51] Int. Cl.⁶ .............................................. A61B 5/04
[52] U.S. Cl. .................................... 128/642; 128/772; 128/692; 607/125
[58] Field of Search ............... 128/639, 642, 772, 692; 606/129, 159; 607/116, 122, 125

[56] References Cited

U.S. PATENT DOCUMENTS

| | | | |
|---|---|---|---|
| 4,682,596 | 7/1987 | Bales et al. | 606/45 |
| 4,920,980 | 5/1990 | Jackowski | 128/642 |
| 4,960,134 | 10/1990 | Webster, Jr. | 607/116 |
| 5,003,990 | 4/1991 | Osypka | 128/772 |

*Primary Examiner*—Lee S. Cohen
*Assistant Examiner*—Brian M. Green
*Attorney, Agent, or Firm*—Kanesaka & Takeuchi

[57] ABSTRACT

An electrophysiology apparatus of the invention is formed of an electrophysiology (EP) catheter and a guide wire. The EP catheter is inserted into a blood vessel along the guide wire. The EP catheter includes a flexible tube having a first passage extending throughout an entire length of the tube, a plurality of electrodes attached to an outer surface of a front area of the tube, and a second passage formed at least inside the front area of the tube. Lead wires extend through the first passage and are connected to the electrodes.

7 Claims, 1 Drawing Sheet

ELECTROPHYSIOLOGY APPARATUS

BACKGROUND OF THE INVENTION AND RELATED ART STATEMENT

The present invention relates to an electrophysiology apparatus, or a combination of an electrophysiology catheter (herein after called "EP catheter") and a guide wire for guiding the EP catheter.

The EP catheter is introduced into a heart of a patient through a blood vessel to access electrical activities within the heart, so that informations for allowing therapeutic interventions are obtained. In one of the conventional EP catheters, a hollow lumen is provided with circular electrodes at a front end of the lumen. Electric conductive leads connected to the electrodes pass inside the lumen and are connected to a suitable machine located outside the patient.

When the EP catheter is used, the catheter is introduced into a desired location of a patient through a blood vessel. Then, electricity is conducted through the electrodes to obtain necessary informations.

However, after the EP catheter is disposed in the blood vessel, it may be required to change a different EP catheter, for example to change the size of the EP catheter or number of the electrodes. In the conventional apparatus, in this situation, the EP catheter must be withdrawn and a new catheter must be inserted again. This exchange takes time and may cause damage to the blood vessel of the patient.

Further, in case the electrodes of the catheter do not properly contact an inside of the blood vessel, the proper electric signal may not be obtained. In this case, the EP catheter must be set or moved once again.

In U.S. Pat. No. 4,762,129, a short tube for guiding a guide wire is attached to the distal end of a long tube having a balloon, wherein a fluid is introduced into the balloon through the long tube. However, no guide system is introduced into the conventional EP catheter.

Accordingly, one object of the invention is to provide an EP catheter having a guide wire to easily exchange the EP catheter as desired.

Another object of the invention is to provide an EP catheter as stated above, wherein lead wires for the electrodes are not substantially electrically affected by the guide wire.

A further object of the invention is to provide an EP catheter as stated above, wherein electrodes attached to the EP catheter can be securely contacted to an inner surface of a blood vessel.

Further objects and advantages of the invention will be apparent from the following description of the invention.

SUMMARY OF THE INVENTION

In accordance with the present invention an electrophysiology apparatus is formed of an EP catheter adapted to be inserted into a blood vessel, and a guide wire for guiding the EP catheter. The EP catheter can be smoothly inserted into the blood vessel by the guide wire.

The EP catheter is formed of a flexible tube having a first passage extending throughout an entire length of the tube, a plurality of electrodes attached to the outer surface of a front area of the tube, and a second passage formed at least inside the front area. Wires connected to the electrodes extend through the first passage. The guide wire passes through the second passage.

When the EP catheter is used, the guide wire is at first introduced into a blood vessel of a patient. Then, the EP catheter is inserted into the blood vessel along the guide wire. Therefore, in case the EP catheter is required to be changed to a different EP catheter having different number of electrodes after insertion of the first EP catheter, it is easy to change to the different EP catheter. Namely, the first EP catheter is removed along the guide wire, and the different EP catheter is inserted again along the guide wire. The blood vessel may not be damaged by the exchange of the catheters.

The guide wire may have a front portion, and a manipulation mechanism for bending the front portion as desired. Thus, the guide wire as well as the EP catheter can be inserted into a desired location.

Further, after the EP catheter is inserted into the proper position in the blood vessel, the guide wire is slightly retracted so that the front portion of the guide wire is located inside the front area of the EP catheter. In this condition, when the guide wire is manipulated to bend the front portion, the front area of the EP catheter is pushed to the inner surface of the blood vessel. Thus, the electrodes formed at the outer surface of the EP catheter is closely contacted to the inner surface of the blood vessel. Even if the EP catheter is smaller than the diameter of the blood vessel, the electrodes can be closely contacted to the blood vessel.

The second passage for the guide wire may be formed of a flexible tubular member extending throughout the entire length of the EP catheter. In this case, if the guide wire is removed, the second passage is used for other purpose, i.e. inserting a fiber scope or dye injection for X-ray filming.

The second passage may be formed of a short tube to extend only at the front area of the catheter. Since the guide wire passes through the short second passage, the short guide wire may be used. Still, the exchange of the EP catheter can be made easily. Also, in case the guide wire is located mostly outside the EP catheter, the electric leads passing through the first passage are not affected by the guide wire.

In case a guiding catheter for guiding the EP catheter and the guide wire is used and the guide wire extends mostly outside the EP catheter, it is preferable that a rear end of the second passage, from which the guide wire exits, is located inside the guiding catheter. Namely, the front area of the EP catheter where the electrodes are fixed is only located outside the guiding catheter. Accordingly, blood vessel is not damaged by the EP wire and the guiding catheter.

DETAILED DESCRIPTION OF PREFERRED EMBODIMENTS

Figure 1:
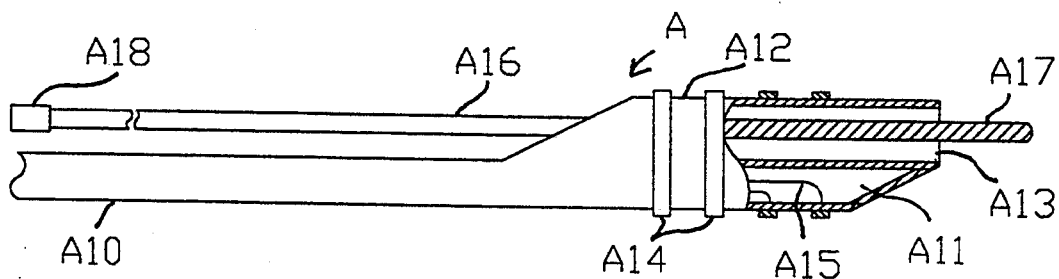
FIG. 1 shows a section view of a main part of a first embodiment of an electrophsiology apparatus or a combination of an EP catheter and a guide wire according to the invention.

In an embodiment A as shown in FIG. 1, an EP catheter is formed of a lumen A10 having a first passage A11 therein, and a guiding portion A12 formed at a front area. The guiding portion A12 has a second passage A13 therein. The diameter of the lumen A10 is enlarged at the front area to receive the guiding portion A12 inside the lumen A10. The first passage A11 is sealed at a front end, while the second passage A13 extends only at the front area and is not sealed.

A plurality of electrodes A14 is attached around an outer surface of the lumen A10 at the front area. Lead wires A15 connected to the electrodes A14 pass through the first passage A11 and exit outside the lumen A10. The lead wires A15 are connected to a suitable device (not shown).

A guide wire A16 used in the present invention includes a front portion A17, and a manipulation portion A18 formed at a rear end of the guide wire A16. When the manipulation portion A18 is manipulated, the front portion A17 is bent in desired directions. The guide wire A16 is known in the art, such as U.S. Pat. No. 3,521,620. Thus, the detailed structure of the guide wire A16 is omitted.

When the EP catheter A is used, the guide wire A16 is inserted into the blood vessel, and then the guiding portion A12 is disposed over the guide wire A16. Thereafter, the lumen A10 is inserted into the blood vessel along the guide wire A16. When the lumen A10 is located in an appropriate position, the lead wires A15 are connected to the outer device, and electricity is conducted through the electrodes A14.

In case the lumen A10 is to be replaced by a different lumen, such as a lumen having a different number of electrodes, the lumen A10 is taken out of the blood vessel, and a new lumen is inserted into the blood vessel along the guide wire A16. In this case, since the guiding portion A12 is located only at the front area of the lumen A10, the lumen A10 can be easily replaced.

The guide wire A16 includes the front portion A17, which can be bent by operation of the manipulating portion A18. Thus, the guide wire A16 can be inserted into a desired location of the blood vessel, by which the EP catheter can be located into the desired location, as well.

Also, in case the electrodes A15 do not properly contact the inner periphery of the blood vessel, the guide wire may be slightly withdrawn so that the front portion A17 is located inside the front area or the guiding portion A12. Then, the manipulating portion A18 is operated to bend the front portion A17. As a result, the electrodes can closely contact the inner periphery of the blood vessel.

Further, in the EP catheter A, the guide wire A16 is located inside the lumen A10 only at the guiding portion A12. The most of the portion of the guide wire A16 is located outside the lumen A10. Thus, the guide wire A16 does not electrically affect the electric leads A15 located inside the first passage A11.

Figure 2:
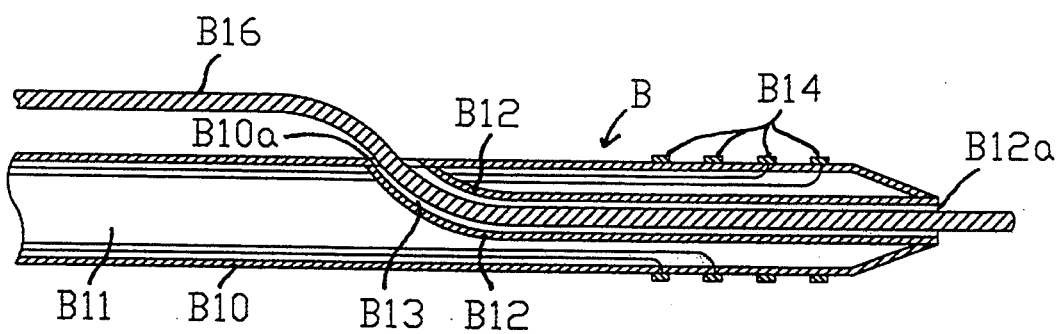
FIG. 2 shows a section view of a main part of a second embodiment of the invention.

FIG. 2 shows a second embodiment B of the EP catheter of the invention. The EP catheter B includes a lumen B10 having a first passage B11 and electrodes B14, and a guiding portion B12 having a second passage B13, as in the EP catheter A. In the EP catheter B, however, the guiding portion B12 is located inside a front area of the lumen B10.

In particular, the guiding portion B12 includes a front end B12a and a rear end B12b. The front end B12a is connected to a front end of the lumen B10 to seal the first passage B11 thereat. The lumen B10 has a side hole B10a, and the rear end B12b is fixed to the lumen B10 around the side hole B10a. A guide wire B16 passes through the guiding portion B12.

In the EP catheter B, since the guiding portion B12 is located inside the lumen B10, the EP catheter can enter into a thin blood vessel. The EP catheter B operates as in the EP catheter A.

Figure 3:
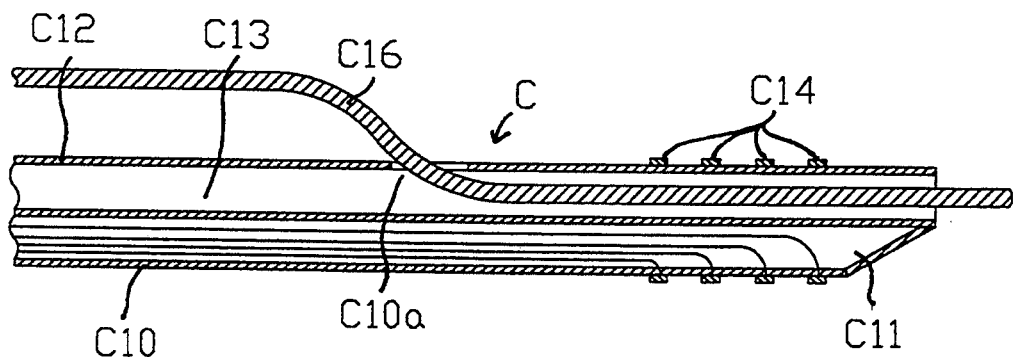
FIG. 3 shows a section view of a main part of a third embodiment of the invention.

FIG. 3 shows a third embodiment C of the EP catheter of the invention. The EP catheter C includes a lumen C10 having a first passage C11 and electrodes C14, and a guiding portion C12 having a second passage C13, as in the EP catheter B. In the EP catheter C, however, the guiding portion C12 extends inside the lumen C10 throughout the entire length thereof, and a side hole C10a is formed.

In the illustrated embodiment, a guide wire C16 enters inside the guide portion C12 from the side hole C10a and exits from the front end. However, the guide wire C16 may extend inside the entire guide portion C12. In the EP catheter C, after the catheter is inserted into the blood vessel, the guide wire C16 may be removed, so that the guide portion C12 may be used for other purpose, such as inserting a fiber scope and exchanging a different guide wire.

In the present invention, the EP catheter can be located in the desired location inside the blood vessel along the guide wire. Also, the EP catheter can be easily exchanged.

While the invention has been explained with reference to the specific embodiments of the invention, the explanation is illustrative and the invention is limited only by the appended claims.

What is claimed is:

1. An electrophysiology apparatus comprising,
an electrophysiology catheter adapted to be inserted into a blood vessel, said catheter including a flexible tube having an outer surface, a front area and a first passage extending throughout an entire length of the tube; a plurality of electrodes with wires, said electrodes being attached to the outer surface of the front area and the wires extending from the electrodes through the first passage; and a second passage formed at least inside the front area of the tube without contacting the wires and being formed of a flexible tubular member extending only at the front area of the catheter, and
a guide wire extending through the second passage of the flexible tube so that the catheter is inserted into the blood vessel through use of the guide wire, said guide wire having a front portion and means for manipulating the front portion of the guide wire so that the electrodes formed at the outer surface of the tube are securely contacted to an inner surface of the blood vessel by bending the front portion of the guide wire.

2. An electrophysiology apparatus according to claim 1, wherein said tube and said tubular member have holes located near the front area and away from the electrodes, said guide wire passing through the tubular member inside the tube and exiting from the holes of the tube and tubular member so that the catheter can be easily removed from the guide wire.

3. An electrophysiology apparatus according to claim 1, wherein said tube includes a hole with an outer edge near the front area, said tubular member having an open rear end being fixed to the outer edge of hole so that the tubular member is located inside the tube at the front area.

4. An electrophysiology apparatus according to claim 3, wherein said tube has a predetermined diameter which does not change throughout an entire length thereof.

5. An electrophysiology apparatus according to claim 3, wherein said tube has a diameter greater at the front area than that at a rest of the tube.

6. An electrophysiology apparatus comprising, an electrophysiology catheter adapted to be inserted into a blood vessel and formed of a flexible tube, said flexible tube having an outer surface, a front area and a first passage extending throughout an entire length of the tube, said first passage having a closed front end; a plurality of electrodes with wires, said electrodes being attached to the outer surface of the front area and the wires extending rearwardly from the electrodes through the first passage; and a second passage situated inside the flexible tube to be separated from the first passage and having an open front end and an open rear end and extending to extend throughout the entire length of the tube from the open front end to the open rear end without contacting the wires, said second passage having a hole located near the front area such that the electrodes are located between the hole and the open front end, and a guide wire extending from the open front end to one of the hole of the second passage and the open rear end so that the guide wire passes at least in the second passage from the open front end to a position corresponding to the hole to guide the catheter, a part of the second passage located between the hole and the open rear end being used for one of guiding the guide wire and providing a material into the blood vessel from the open rear end.

7. An electrophysiology apparatus according to claim 6, wherein said guide wire extends only through the portion between the open front end and the hole so that the catheter can be exchanged easily, the part of the second passage between the hole and the open rear end being used for at least one of inserting a fiber scope and a dye injection for x-ray filming.

* * * * *